US006659954B2

(12) United States Patent
Robinson

(10) Patent No.: US 6,659,954 B2
(45) Date of Patent: Dec. 9, 2003

(54) MICROMACHINED ULTRASOUND TRANSDUCER AND METHOD FOR FABRICATING SAME

(75) Inventor: Andrew L. Robinson, Bellevue, WA (US)

(73) Assignee: Koninklijke Philips Electronics NV, Eindhoven (NL)

(*) Notice: Subject to any disclaimer, the term of this patent is extended or adjusted under 35 U.S.C. 154(b) by 0 days.

(21) Appl. No.: 10/036,281

(22) Filed: Dec. 19, 2001

(65) Prior Publication Data

US 2003/0114760 A1 Jun. 19, 2003

(51) Int. Cl.[7] .................................................. A61B 8/00
(52) U.S. Cl. ...................................... 600/459; 29/25.35
(58) Field of Search ................................ 600/459, 140; 367/140, 162, 173–174, 178; 29/25.35

(56) References Cited

U.S. PATENT DOCUMENTS

| | | | | |
|---|---|---|---|---|
| 5,406,163 A | | 4/1995 | Carson et al. | 310/334 |
| 5,488,954 A | | 2/1996 | Sleva et al. | 128/662.03 |
| 5,619,476 A | | 4/1997 | Haller et al. | 367/181 |
| 5,870,351 A | | 2/1999 | Ladabaum et al. | 367/163 |
| 5,894,452 A | | 4/1999 | Ladabaum et al. | 367/163 |
| 5,956,292 A | | 9/1999 | Bernstein | 367/140 |
| 5,982,709 A | | 11/1999 | Ladabaum et al. | 367/170 |
| 6,004,832 A | | 12/1999 | Haller et al. | 438/50 |
| 6,049,158 A | | 4/2000 | Takeuchi et al. | 310/328 |
| 6,115,326 A | | 9/2000 | Puma et al. | 367/118 |
| 6,271,620 B1 | * | 8/2001 | Ladabaum | 310/334 |
| 6,295,247 B1 | * | 9/2001 | Khuri-Yakub et al. | 367/140 |
| 6,314,057 B1 | * | 11/2001 | Solomon et al. | 367/174 |
| 6,381,197 B1 | * | 4/2002 | Savord et al. | 367/178 |
| 6,426,582 B1 | * | 7/2002 | Niederer et al. | 310/309 |
| 6,430,109 B1 | * | 8/2002 | Khuri-Yakub et al. | 367/181 |
| 2002/0048219 A1 | * | 4/2002 | Ladabaum et al. | 367/162 |

OTHER PUBLICATIONS

Jin, X. C. et al., "Surface Micromachined Capacitive Ultrasonic Immersion Transducers," IEEE, pp. 649–654, 1998.

Jin, X. C. et al., "The Microfabrication of Capacitive Ultrasonic Transducers," IEEE, pp. 437–440, Jun. 1997.

Jin, Wuecheng et al.,"The Microfabrication of Capacitive Ultrasonic Transducers," Journal of Microelectromechanical Systems, IEEE/ASME Publication, vol. 7, No. 3, pp. 295–302, Sep. 1998.

Haller, Matthew I., and Khuri–Yakub, Butrus T., "A Surface Micromachined Electrostatic Ultrasonic Air Transducer," IEEE Ultrasonics, vol. 43, No. 1, pp. 1–6, Jan. 1996.

Schindel, David W., and Hutchins, David A., "The Design and Characterization of Micromachined Air–Coupled Capacitance Transducers," IEEE Ultrasonics, vol. 42, No. 1, pp. 42–50, Jan. 1995.

(List continued on next page.)

*Primary Examiner*—Francis J. Jaworski
(74) *Attorney, Agent, or Firm*—Dorsey & Whitney LLP

(57) ABSTRACT

The invention is directed towards improved structures for use with micro-machined ultrasonic transducers (MUTs), and methods for fabricating the improved structures. In one embodiment, a MUT on a substrate includes an acoustic cavity formed within the substrate at a location below the MUT. The cavity is filled with an acoustic attenuation material to absorb acoustic waves in the substrate, and to reduce parasitic capacitance. In another embodiment, the cavity is formed below a plurality of MUTs, and filled with an attenuation material. In still another embodiment, an attenuation material substantially encapsulates a plurality of MUTs on a dielectric layer. In yet other embodiments, at least one monolithic semiconductor circuit is formed in the substrate that may be operatively coupled to the MUTs to perform signal processing and/or control operations.

48 Claims, 7 Drawing Sheets

OTHER PUBLICATIONS

Jin, Xuecheng et al., "Fabrication and Characterization of Surface Micromachined Capacitive Ultrasonic Immersion Transducers," IEEE Journal of Microelectromechanical Systems, vol. 8, No. 1, pp. 100–114, Mar. 1999.

Eccardt, Peter–Christian et al., "Surface micromachined ultrasound transducer in CMOS technology," IEEE Ultrasonics Symposium, pp. 959–962, 1996.

Ladabaum, I. et al., "Microfabricated Ultrasonic Transducers: Towards Robust Models and Immersion Devices," IEEE Ultrasonics Symposium, pp. 335–338, 1996.

Ladabaum, Igal et al., "Surface Micromachined Capacitive Ultrasonic Transducers,"IEEE, Transactions on Ultrasonics, Ferroelectrics, and Frequency Control, vol. 45, No. 3, pp. 678–690, May 1998.

Suzuki, Kenichiro et al., "A Silicon Electrostatic Ultrasonic Transducer," IEEE Transactions on Ultrasonics, Ferroelectrics, and Frequency Control, vol. 36, No. 6, pp. 620–627, Nov. 1989.

Haller, Matthew I. and Khuri–Yakub, Butrus T., "A Surface Micromachined Electrostatic Ultrasonic Air Transducer," IEEE Ultrasonics Symposium, pp. 1241–1244, 1994.

Oralkan, Ö. et al., "Simulation and Experimental Characterization of a 2–D, 3–MHZ Capacitive Micromachined Ultrasonic Transducer (CMUT) Array Element," date unknown.

Ladabaum, I. et al., "Micromachined Ultrasonic Transducers (MUTs)," IEEE Ultrasonics Symposium, pp. 501–504, 1995.

Sensant Corporation, "Silicon Ultrasound™: Sensant's Breakthrough Transducers for Medical Imaging," advertisement, 1999.

* cited by examiner

MICROMACHINED ULTRASOUND TRANSDUCER AND METHOD FOR FABRICATING SAME

TECHNICAL FIELD

This invention relates generally to ultrasound diagnostic systems that use ultrasonic transducers to provide diagnostic information concerning the interior of the body through ultrasound imaging, and more particularly, to micromachined ultrasonic transducers used in such systems.

BACKGROUND OF THE INVENTION

Ultrasonic diagnostic imaging systems are in widespread use for performing ultrasonic imaging and measurements. For example, cardiologists, radiologists, and obstetricians use ultrasonic diagnostic imaging systems to examine the heart, various abdominal organs, or a developing fetus, respectively. In general, imaging information is obtained by these systems by placing an ultrasonic probe against the skin of a patient, and actuating an ultrasonic transducer located within the probe to transmit ultrasonic energy through the skin and into the body of the patient. In response to the transmission of ultrasonic energy into the body, ultrasonic echoes emanate from the interior structure of the body. The returning acoustic echoes are converted into electrical signals by the transducer in the probe, which are transferred to the diagnostic system by a cable coupling the diagnostic system to the probe.

Acoustic transducers commonly used in ultrasonic diagnostic probes are comprised of an array of individual piezoelectric elements formed from a piezoelectric material by the application of a number of meticulous manufacturing steps. In one common method, a piezoelectric transducer array is formed by bonding a single block of piezoelectric material to a backing member that provides acoustic attenuation. The single block is then laterally subdivided by cutting or dicing the material to form the rectangular elements of the array. Electrical contact pads are formed on the individual elements using various metallization processes to permit electrical conductors to be coupled to the individual elements of the array. The electrical conductors are then coupled to the contact pads by a variety of electrical joining methods, including soldering, spot-welding, or by adhesively bonding the conductor to the contact pad.

Although the foregoing method is generally adequate to form acoustic transducer arrays having up to a few hundred elements, larger arrays of transducer elements having smaller element sizes are not easily formed using this method. Consequently, various techniques used in the fabrication of silicon microelectronic devices have been adapted to form ultrasonic transducer elements, since these techniques generally permit the repetitive fabrication of small structures in intricate detail.

An example of a device that may be formed using semiconductor fabrication methods is the micro-machined ultrasonic transducer (MUT). The MUT has several significant advantages over conventional piezoelectric ultrasonic transducers. For example, the structure of the MUT generally offers more flexibility in terms of optimization parameters than is typically available in conventional piezoelectric devices. Further, the MUT may be conveniently formed on a semiconductor substrate using various semiconductor fabrication methods, which advantageously permits the formation of relatively large numbers of transducers, which may then be integrated into large transducer arrays. Additionally, interconnections between the MUTs in the array and electronic devices external to the array may also be conveniently formed during the fabrication process. MUTs may be operated capacitively, and are referred to as cMUTs, as shown in U.S. Pat. No. 5,894,452. Alternatively, piezoelectric materials may be used to fabricate the MUT, which are commonly referred to as pMUTs, as shown in U.S. Pat. No. 6,049,158. Accordingly, the MUT has increasingly become an attractive alternative to conventional piezoelectric ultrasonic transducers in ultrasound systems.

FIG. 1 is a partial cross sectional view of a MUT 1 according to the prior art. The MUT 1 may have a platform that is rectangular, circular, or may be of other regular shapes. The MUT 1 generally includes an upper surface 2 that is spaced apart from a lower surface 3 that abuts a silicon substrate 5. Alternatively, a dielectric layer 4 may be formed on the substrate 5 that underlies the MUT 1. When a time-varying excitation voltage (not shown) is applied to the MUT 1, a vibrational deflection in the upper surface 2 is developed that stems from the electro-mechanical properties of the MUT 1. Accordingly, acoustic waves 6 are created that radiate outwardly from the upper surface 2 in response to the applied time-varying voltage. The electro-mechanical properties of the MUT 1 similarly allow the MUT 1 to be responsive to deflections resulting from acoustic waves 7 that impinge on the upper surface 2.

One disadvantage in the foregoing prior art device is that a portion of the ultrasonic energy developed by the MUT 1 may be projected backwardly into the underlying substrate 5, rather that being radiated outwardly in the acoustic wave 6, which results in a partial loss of radiated energy from the MUT 1. Moreover, when ultrasonic energy is coupled into the underlying substrate 5, various undesirable effects are produced, which are briefly described below.

With reference now to FIG. 2, a partial cross sectional view of a MUT array 10 according to the prior art is shown. The array 10 includes a plurality of MUT transducers 1 formed on a silicon substrate 5. Each transducer 1 is coupled to a time-varying voltage source through a plurality of electrical interconnections formed in the substrate 5. For clarity of illustration, the voltage source and the electrical interconnections are not shown. An acoustic wave 21 may be conducted into the substrate 5 through a back surface 3. The wave 21 propagates within the substrate 5 and is internally reflected at a lower surface 18 of the substrate 5 to form a reflected wave 23 that is directed towards an upper surface 19 of the substrate 5. Consequently, a plurality of reflected waves 23 propagate within the substrate 5 between the upper surface 19 and the lower surface 18. A portion of the energy present in each reflected wave 23 may also leave the substrate 5 through the surface 18, to form a plurality of leakage waves 25. An internal reflection 27 from an end 24 of the array 10 may lead to still further reflected waves 27 and leakage waves 26.

The propagation of acoustic waves 23 and 27 in the substrate 5, as described above, permits ultrasonic energy to be cross-coupled between the plurality of MUT transducers 1 on the substrate 5 and produce undesirable "cross-talk" signals between the plurality of MUTs 1, as well as other undesirable interference effects. Still further, the internal reflection of waves in the substrate 5 may adversely affect the acceptance angle, or directivity of the array 10.

Various prior art devices have included elements that impede the propagation of waves in the substrate. For example, one prior art device employs a plurality of trenches between the MUTs 1 that extend downwardly into the substrate 5 to interrupt wave propagation within the substrate 5. Another prior art device employs a similar downwardly projecting trench, and fills the trench with an acoustic absorbing material in order to at least partially absorb the energy in the reflected waves 23. Other prior art devices minimize lateral wave propagation by controlling still other geometrical details of the array. Although these prior art devices generally reduce the undesired lateral wave propagation in the substrate, they generally limit the design flexibility inherent in the MUT by reducing the number of design parameters that may be independently varied. Furthermore, the additional manufacturing steps significantly increase the manufacturing cost of arrays that use MUTs.

A further disadvantage associated with the prior art devices shown in FIGS. 1 and 2 is that a relatively large parasitic capacitance may be formed between the one or more MUTs 1 and the underlying substrate 5. Since the MUT 1 is an electro-mechanical device that is generally excited by frequencies in the megahertz range, the formation of parasitic capacitances between the MUTs 1 and the substrate 5 further degrade the performance of the MUTs 1 by producing an additional capacitive load that generally degrades the sensitivity of the MUT.

Accordingly, there is a need in the art for micro-machined ultrasonic transducer structures that are capable of producing significant reductions in acoustic wave propagation in the underlying substrate. Further, there is a need in the art for a micro-machined ultrasonic transducer structures that suppress parasitic capacitive coupling between a MUT and an underlying substrate.

SUMMARY OF THE INVENTION

The invention is directed towards improved structures for use with micro-machined ultrasonic transducers (MUTs), and methods for fabricating the improved structures. In one aspect, a MUT is formed on a substrate and an acoustic cavity is formed within the substrate at a location below the MUT. The acoustic cavity is filled with an acoustic attenuation material to absorb acoustic waves propagated into the substrate, and to reduce the effect of parasitic capacitances on the operation of the MUT. In another aspect, the acoustic cavity is formed below a plurality of MUTs that comprise an array. The acoustic cavity and the acoustic attenuation material substantially reduce cross coupling between the MUTs by preventing wave propagation in the substrate. In still another aspect, a plurality of MUTs abut a dielectric layer with the MUTs being substantially encapsulated by the acoustic attenuation material. In yet another aspect, at least one monolithic semiconductor circuit is formed in the substrate that may be operatively coupled to the MUTs, the circuit being positioned in a non-etched portion of the substrate. In still another aspect, the at least one monolithic semiconductor circuit is formed in the substrate and positioned in a thin substrate layer above the acoustic cavity. In yet another aspect, a plurality of MUTs is attached to one side of a layer of semiconductor material, and a dielectric layer is formed on the opposing side. At least one monolithic semiconductor circuit is formed in the semiconductor material that may be operatively coupled to the MUTs.

DETAILED DESCRIPTION OF THE INVENTION

The present invention is generally directed to ultrasound diagnostic systems that use micro-machined ultrasonic transducers (MUTs) to provide diagnostic information concerning the interior of the body through ultrasound imaging. Many of the specific details of certain embodiments of the invention are set forth in the following description and in FIGS. 3 through 16 to provide a thorough understanding of such embodiments. One skilled in the art will understand, however, that the present invention may be practiced without several of the details described in the following description. Further, it is understood that the MUT described in the embodiments below may include any electro-mechanical device that may be formed on a semiconductor substrate that is capable of emitting acoustic waves when excited by a time-varying voltage, and producing a time-varying electrical signal when stimulated by acoustic waves. Accordingly, the MUT may include a capacitive micro-machined ultrasonic transducer (cMUT), a piezoelectric micro-machined ultrasonic transducer (pMUT), or still other micro-machined ultrasonic devices. Moreover, in the description that follows, it is understood that the figures related to the various embodiments are not to be interpreted as conveying any specific or relative physical dimension, and that specific or relative dimensions related to the various embodiments, if stated, are not to be considered limiting unless the claims expressly state otherwise.

Figure 1:
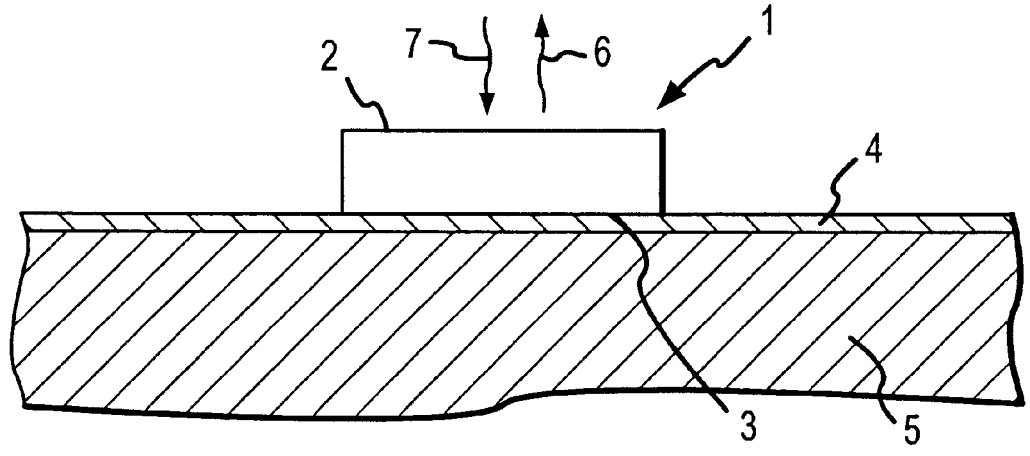
FIG.1 (PRIOR ART)
FIG. 1 is a partial cross sectional view of a MUT transducer according to the prior art.
Figure 2:
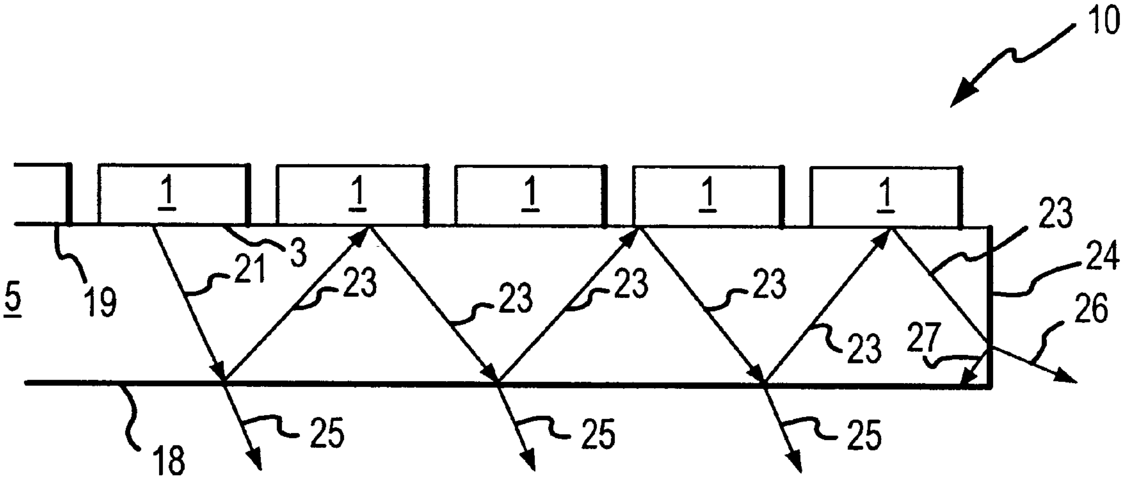
FIG.2 (PRIOR ART)
FIG. 2 is a partial cross sectional view of a MUT transducer array according to the prior art.
Figure 3:
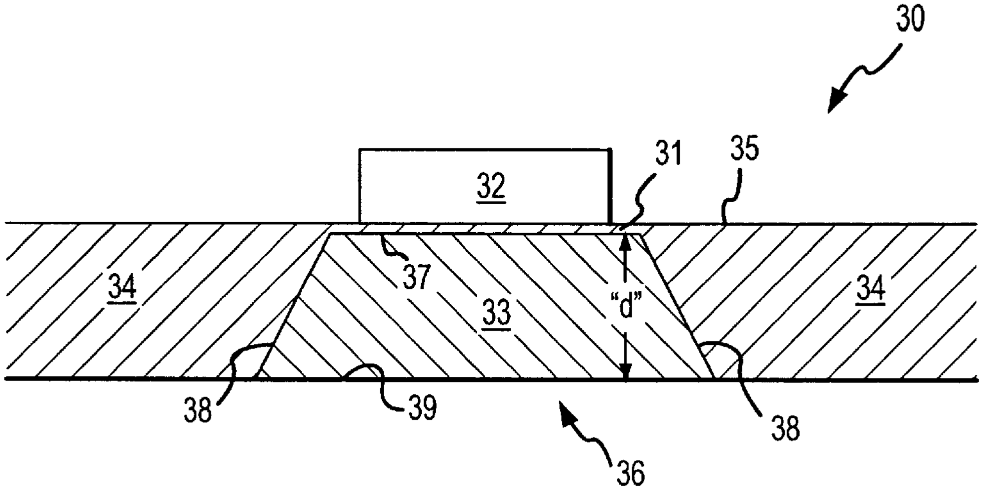
FIG. 3 is a partial cross sectional view of a MUT transducer assembly according to an embodiment of the invention.

FIG. 3 is a partial cross sectional view of a MUT transducer array 30 according to an embodiment of the invention. The MUT transducer array 30 includes a MUT 32 formed on a substrate 34. The array 30 is capable of receiving ultrasonic waves and generating an output electrical signal, and generating ultrasonic waves in response to input electrical signals. The input and output signals are exchanged with an ultrasound system (not shown) through a plurality of interconnections positioned within the substrate 34. For clarity of illustration, the interconnecting portions are not shown in FIG. 3. The MUT 32 may be formed on the substrate 34 through the application of a series of well-known semiconductor fabrication processes. For example, the MUT 32 may be formed by patterning a surface of the substrate using a photolithographic process, and successively adding material layers to the substrate 34 by various material deposition processes. Structural features of the MUT 32 may further be formed by removing selected portions of the deposited material through the application of various etching processes. A dielectric layer may optionally be formed on an upper substrate surface 35 that electrically isolates the MUT 32 from the underlying substrate 34. Alternatively, the dielectric layer may be incorporated directly into the MUT 32.

Still referring to FIG. 3, the array 30 further includes a cavity 36 that is formed within the substrate 34. The cavity 36 extends from an upper cavity surface 37 and proceeds downwardly towards a lower substrate surface 39. The cavity 36 also includes a pair of sidewalls 38 that depend downwardly from the upper cavity surface 37 to the lower substrate surface 39. The upper cavity surface 37 is separated from the upper surface 35 by a separation layer 31 that is sufficiently thin to prevent the significant propagation of acoustic waves to other portions of the substrate 34. The cavity 36 may be filled with an acoustic attenuation material 33 having a relatively high acoustic attenuation to provide an acoustically-damped region below the MUT 32. The dimensions of the cavity 36 and the characteristics of the material 33 cooperatively yield an acoustic impedance that is compatible with the overall acoustic design of the array 30. For example, the depth "d" of the cavity 36 may be sufficient to allow waves transmitted from the MUT 32 through the surface 35 to be attenuated to a relatively negligible level, since the material 33 is sufficiently lossy to dissipate the acoustic energy present in the waves. Accordingly, the material 33 may include an elastomeric material, such as a room temperature vulcanizing (RTV) elastomer, or various epoxy matrices having dispersed solid metallic, ceramic, or polymeric filler particles of a selected density. Still further, the epoxy matrix may be filled with elastomeric particles or air-filled "micro-balloons" to achieve the desired acoustic properties. The array 30 may be positioned on an acoustic backing member (not shown) to support the array 30 and to provide further acoustic attenuation.

Figure 4:
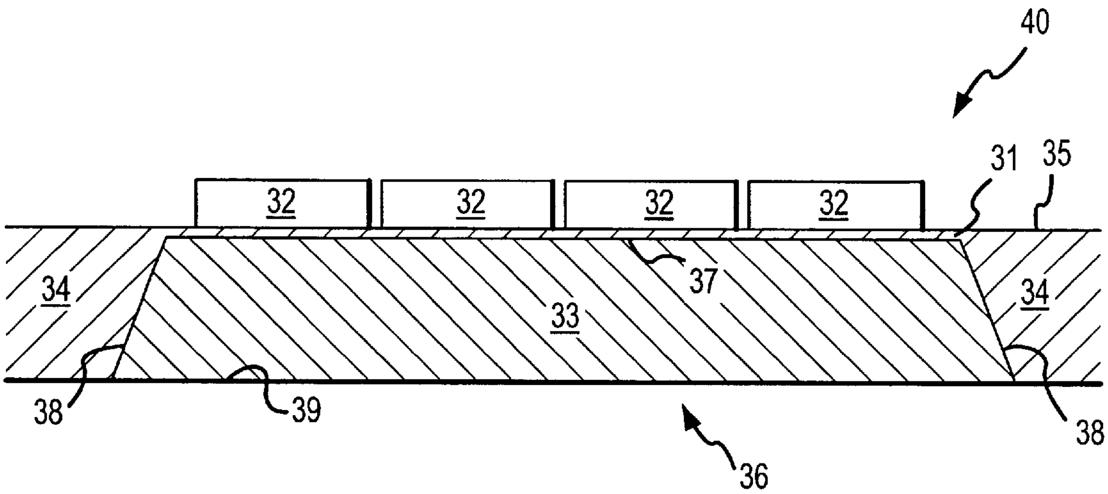
FIG. 4 is a partial cross sectional view of a MUT transducer array according another embodiment of the invention.

FIG. 4 is a partial cross sectional view of a MUT transducer array 40 according to another embodiment of the invention. The MUT transducer array 40 includes a plurality of MUTs 32 formed on a substrate 34 in a predetermined pattern to form the array 40. A cavity 36 is formed below the plurality of MUTs 32 that extends downwardly from an upper cavity surface 37 towards a lower substrate surface 39. The cavity 36 is dimensioned to yield a predetermined acoustic impedance when the cavity 36 is filled with a selected acoustic material 33.

Figure 5:
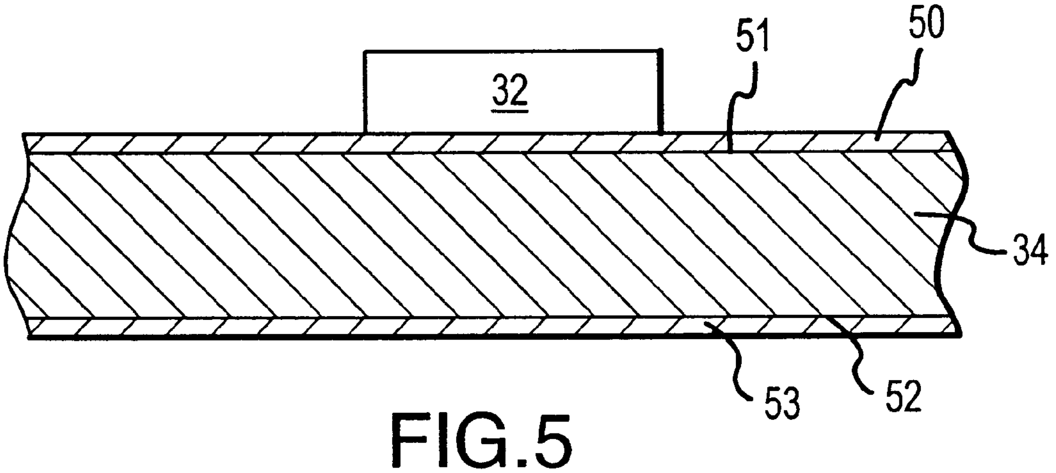
FIG. 5 is a partial cross sectional view of a MUT transducer illustrating a step in a method of fabricating the MUT transducer according to still another embodiment of the invention.

FIGS. 5 through 8 are partial cross sectional views that illustrate the steps in a method for fabricating a MUT array according to another embodiment of the invention. Referring to FIG. 5, a MUT 32 is formed on a substrate 34 by a sequence of well-known semiconductor fabrication steps, which may include the formation of a dielectric layer 50 on an upper surface 51 of the substrate 34. The dielectric layer 50 may include silicon dioxide or silicon nitride, although other dielectric materials including silicon oxynitrides may be used. A layer 53 of silicon dioxide or silicon nitride is deposited on a lower surface 52. The layer 53 is patterned using standard photolithographic processes to create an opening in the layer 53, providing access to the back surface 52 of the substrate 34.

Figure 6:
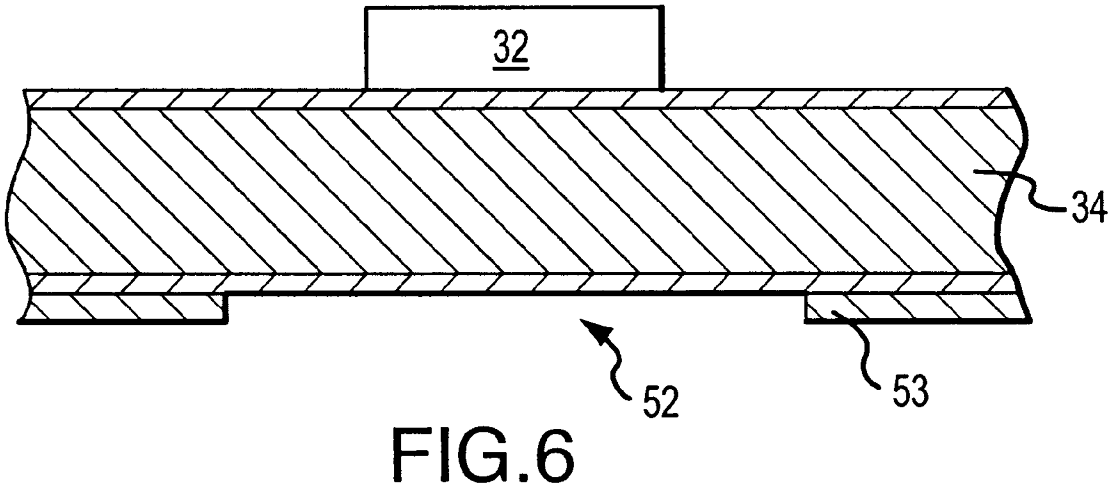
FIG. 6 is a partial cross sectional view of a MUT transducer illustrating a step in a method of fabricating the MUT transducer according to still another embodiment of the invention.
Figure 7:
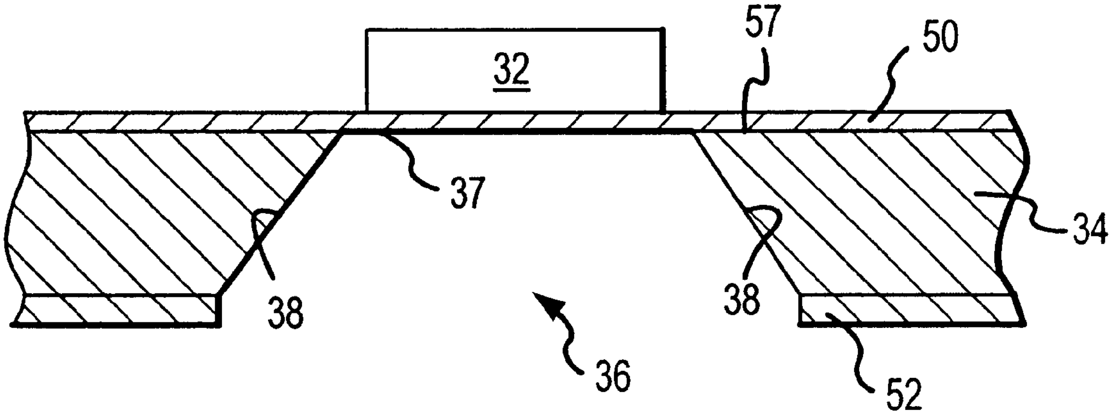
FIG. 7 is a partial cross sectional view of a MUT transducer illustrating a step in a method of fabricating the MUT transducer according to still another embodiment of the invention.

Turning now to FIG. 6, the substrate 34 may then be etched to form a cavity 36 that extends from the lower surface 52 to an upper cavity surface 37, as shown in FIG. 7. The dielectric layer 50 may also serve as an etch stop layer during the etching process, although other etch stop devices, such as selective doping of the substrate 34, may also be used. The substrate 34 may be etched using a variety of isotropic or anisotropic solutions in an etching bath to form the cavity 36. The material properties of the substrate 34 and the composition of the etching bath generally cooperatively determine the shape of the cavity 36. For example, if the substrate 34 is monocrystalline silicon having a <111> crystalline orientation, then an etching solution comprised of hydrofluoric acid and nitric acid will form a cavity 36 having side walls 38 that extend inwardly at approximately 45 degrees. Alternatively, a <100> monocrystalline material etched with a potassium hydroxide etching solution will yield side walls that extend inwardly at approximately 54.7 degrees. Other internal shapes for the cavity 36 may be obtained using other crystalline configurations in the substrate 34 together with other etching solutions, and are considered to be within the scope of the invention. Similarly, methods other than wet etching may be used to form the cavity 36. For example, dry etching methods, which include plasma etching, ion beam milling and reactive ion etching may be also used.

Figure 8:
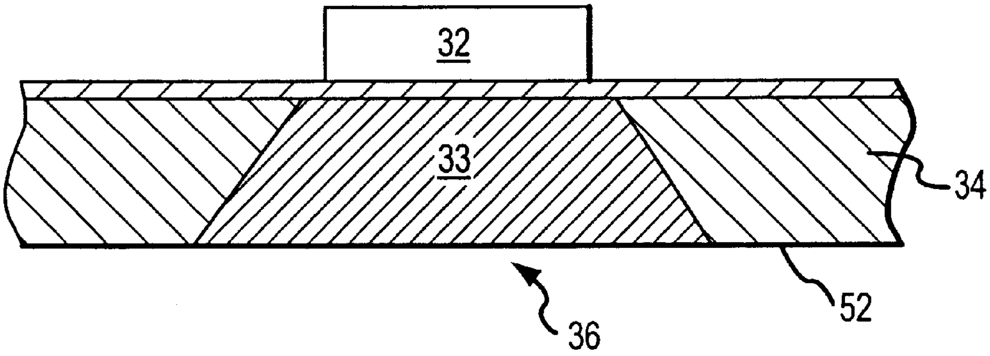
FIG. 8 is a partial cross sectional view of a MUT transducer illustrating a step in a method of fabricating the MUT transducer according to still another embodiment of the invention.

Referring now to FIG. 8, the cavity 36 may be filled with an acoustic material 33, which may be comprised of any of the materials identified above. The material 33 may be deposited into the acoustic cavity 36 by direct injection of the material 33 into the cavity 36, although other methods exist. For example, the material 33 may be sprayed into the cavity 36. Following the application of the material 33, the layer 53 may be stripped to expose the surface 52. The layer 53 may be stripped using various stripping methods, including wet chemical stripping or plasma stripping methods. An acoustic backing member may be positioned below the array to provide further acoustic attenuation.

The foregoing embodiments advantageously provide an acoustic cavity below the one or more MUT devices that is filled with an acoustic material to substantially inhibit the propagation of acoustic waves in the substrate. Additionally, the attenuation material generally possesses an acoustic impedance that substantially differs from the substrate material, permitting the MUT to transmit and receive ultrasonic signals more effectively. Still further, by positioning the substantially non-electrically conductive attenuation material below the one or more MUTs, parasitic capacitive coupling effects that may adversely affect the performance of the MUTs are reduced.

Figure 9:
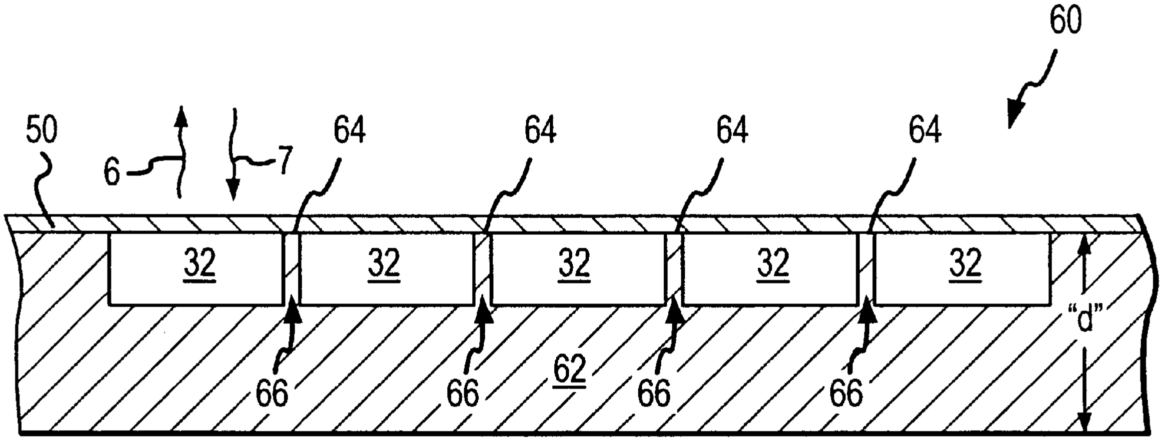
FIG. 9 is a partial cross sectional view of a MUT transducer array according still another embodiment of the invention.

FIG. 9 is a partial cross sectional view of a MUT transducer array 60 according still another embodiment of the invention. The array 60 includes a plurality of MUTs 32 that are attached to a dielectric layer 50. The MUTs 32 are further embedded in an acoustic attenuation material 62 that substantially encapsulates the MUTs 32 and abuts the dielectric layer 50 at locations 64. The material 62 further substantially fills spaces 66 between adjacent MUTs 32 to provide additional resistance to cross-coupling effects. The acoustic attenuation material 62 extends a distance "d" below the layer 50 to ensure that waves propagated into the material 62 are substantially attenuated.

Still referring to FIG. 9, the dielectric layer 50 is a thin structure that permits acoustic waves 6 generated by each of the MUTs 32 in the array 60 to be transmitted outwardly, and correspondingly permits reflected acoustic waves 7 to be received by the MNTs 32. Accordingly, the layer 50 may be comprised of a thin layer of silicon dioxide or silicon nitride, although other alternatives exist.

Figure 10:
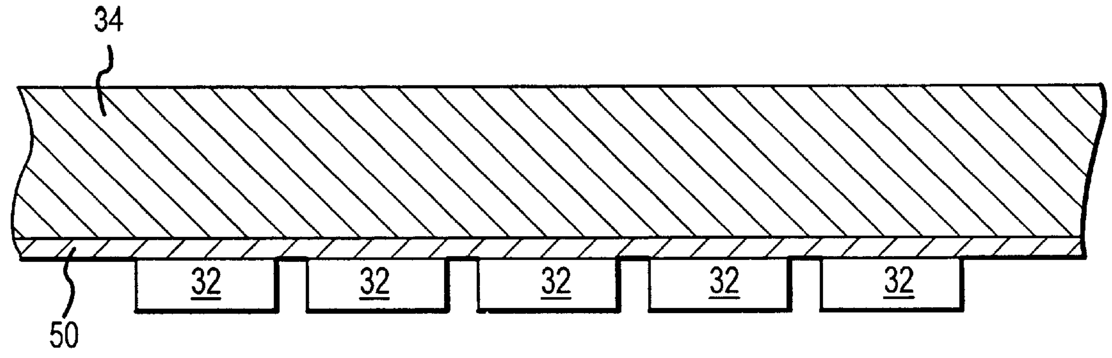
FIG. 10 is a partial cross sectional view of a MUT transducer illustrating a step in a method of fabricating the MUT transducer according to still yet another embodiment of the invention.
Figure 11:
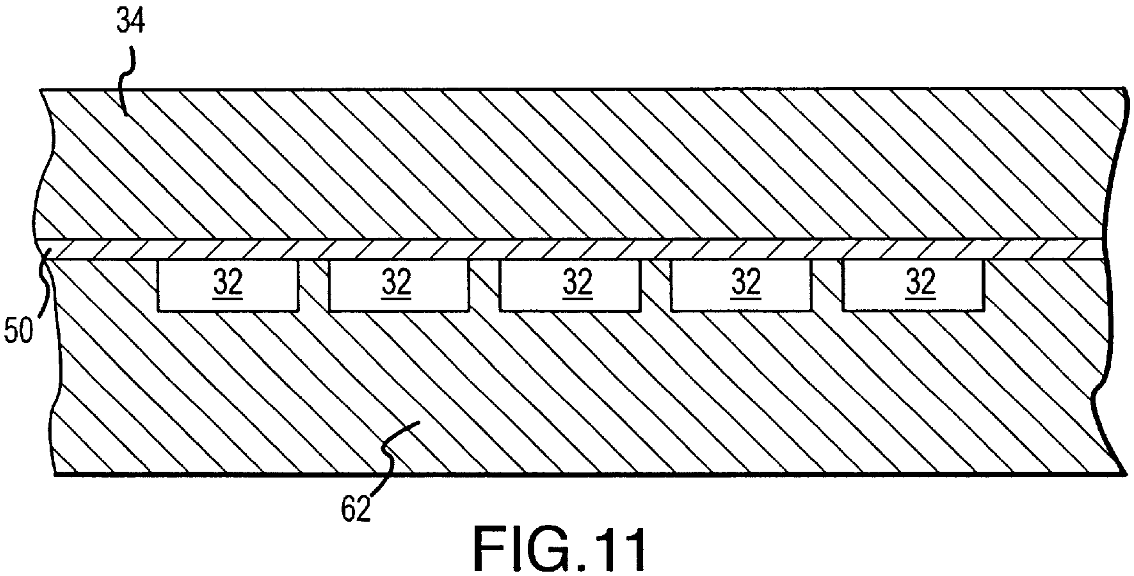
FIG. 11 is a partial cross sectional view of a MUT transducer illustrating a step in a method of fabricating the MUT transducer according to still yet another embodiment of the invention.
Figure 12:
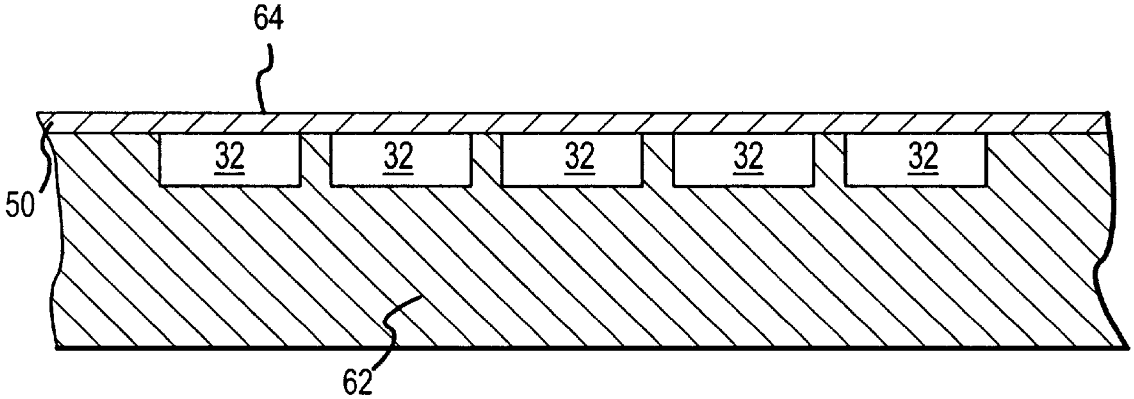
FIG. 12 is a partial cross sectional view of a MUT transducer illustrating a step in a method of fabricating the MUT transducer according to still yet another embodiment of the invention.

FIGS. 10 through 12 are partial cross sectional views that illustrate the steps in a method for fabricating a MUT array according to another embodiment of the invention. Referring to FIG. 10, a dielectric layer 50 is formed on a substrate 34. A plurality of MUTs 32 are similarly formed on the substrate 34, with the dielectric layer 50 interposed between the MUTs 32 and the substrate 34. Alternatively, the substrate 34 may be comprised of a silicon-on-insulator (SOI) substrate that includes a layer of dielectric material that is spaced apart from the MUTs 32 and positioned within the substrate 32, so that the MUTs 32 are positioned directly on a silicon surface. An acoustic attenuation material 62 is formed over the plurality of MUTs 32 that substantially encapsulates the MUTs 32, as shown in FIG. 11.

Turning to FIG. 12, the substrate 34 is substantially removed to expose an upper dielectric surface 64. If the substrate 34 is an SOI substrate, then the substrate 34 is thinned to expose the insulating layer. In either case, the substrate 34 may be removed by wet etching the substrate 34 in a suitable solution, although other alternative methods exist. For example, the substrate 34 may be removed by employing wet spin etching to remove the substrate 34. The substrate 34 may also be removed by backgrinding the substrate 34 to expose the surface 64.

In addition to the advantages previously identified in connection with other embodiments, the foregoing embodiments additionally provide an unbounded acoustic cavity that advantageously permits the entire MUT to be encapsulated, so that spaces between adjacent MUTs are filled with the acoustic attenuation material, thus further reducing cross-coupling effects.

Figure 13:
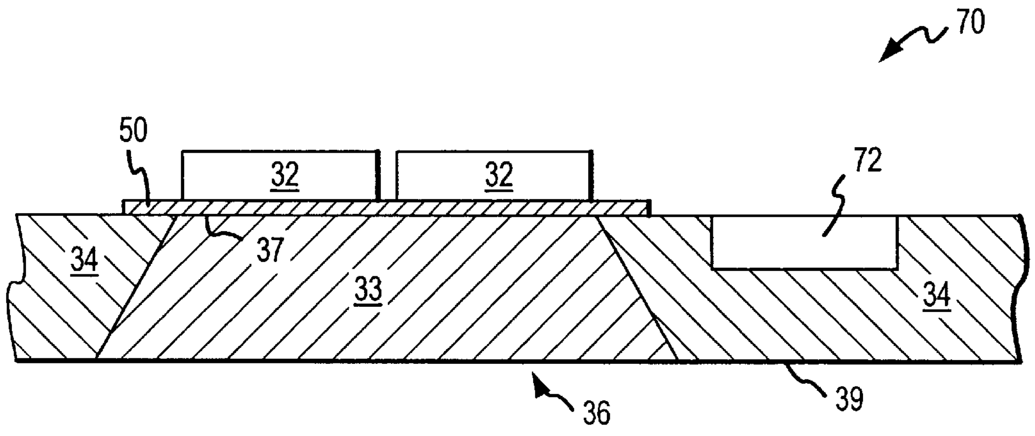
FIG. 13 is a partial cross sectional view of a MUT transducer array according another embodiment of the invention.

FIG. 13 is a partial cross sectional view of a MUT transducer array 70 according another embodiment of the invention. The MUT transducer array 70 includes a plurality of MUTs 32 formed on a substrate 34 in a predetermined pattern. A dielectric layer 50 may be interposed between the plurality of MUTs 32 and the substrate 34 to provide electrical isolation. An attenuation cavity 36 is formed below the plurality of MUTs 32 that extends downwardly from an upper cavity surface 37 towards a lower substrate surface 39. The cavity 36 may be filled with an acoustic attenuation material 33 to yield selected acoustic properties for the array 70. The array 70 further includes at least one semiconductor circuit 72 that is monolithically formed in the substrate 34 that is positioned proximate to a side of the attenuation cavity 36. The circuit 72 may include a single semiconductor device, such as a field effect transistor (FET) or a similar device, which is used to drive the MUTs. Alternatively, the circuit 72 may comprise more fully integrated devices. For example, the circuit 72 may include monolithically formed circuits that at least partially perform receiver functions, beamforming processing, or other "front end" processing for the array 70. Further, the circuit 72 may also include circuits that perform control operations for the array 70. The semiconductor circuit 72 may be interconnected with the plurality of MUTs 32 and to other circuits external to the array by interconnecting elements formed in the substrate (not shown). The MUT transducer array 70 may be positioned on an acoustic backing member (not shown) to support the array 70 and to provide further acoustic attenuation.

Figure 14:
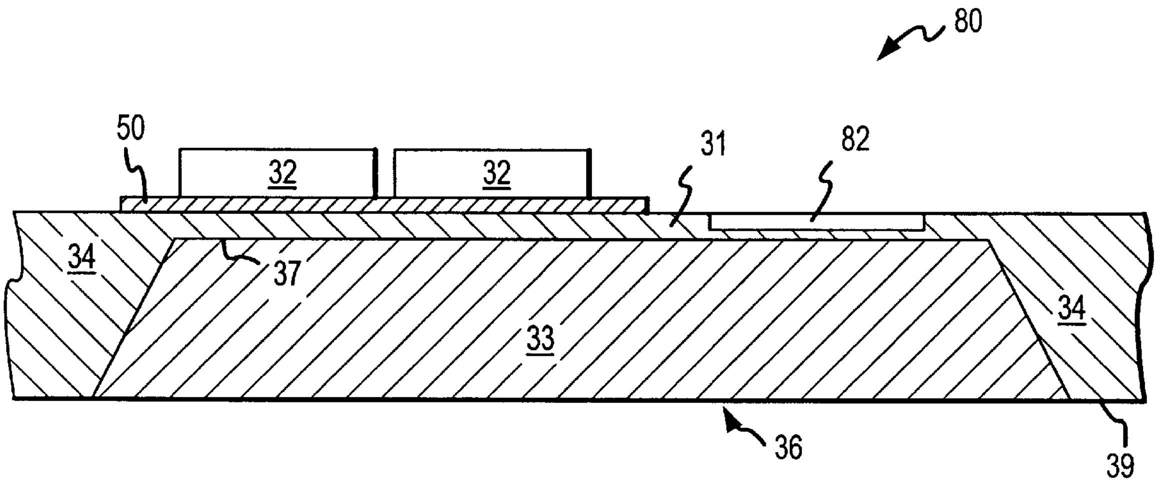
FIG. 14 is a partial cross sectional view of a MUT transducer array according yet another embodiment of the invention.

FIG. 14 is a partial cross sectional view of a MUT transducer array 80 according yet another embodiment of the invention. The MUT transducer array 80 includes a plurality of MUTs 32 formed on a substrate 34, which may have a dielectric layer 50 interposed between the plurality of MUTs 32 and the substrate 34. An attenuation cavity 36 is formed below the plurality of MUTs 32 that extends downwardly from an upper cavity surface 37 towards a lower substrate surface 39. The cavity 36 may be filled with an acoustic attenuation material 33 to yield selected acoustic properties for the array 80. The array 80 further includes at least one semiconductor circuit 82 that is monolithically formed in a separation layer 31 at a location above the attenuation cavity 36, and proximate to the plurality of MUTs 32. As in the previous embodiment, the circuit 82 may include a single semiconductor device, or the circuit 82 may comprise more fully integrated devices. The semiconductor circuit 82 may be interconnected with the plurality of MUTs 32 and to other circuits external to the array by interconnection elements formed in the substrate (not shown). Alternatively, at least one circuit 82 may be formed in the separation layer 31 at a position approximately below the plurality of MUTs 32 and form interconnections (not shown) with the MUTs 32 through vias (also not shown) that extend from the MUTs 32 to the at least one circuit 82. The MUT transducer array 80 may be positioned on an acoustic backing member (not shown) to support the array 80 and to provide still further acoustic attenuation.

Figure 15:
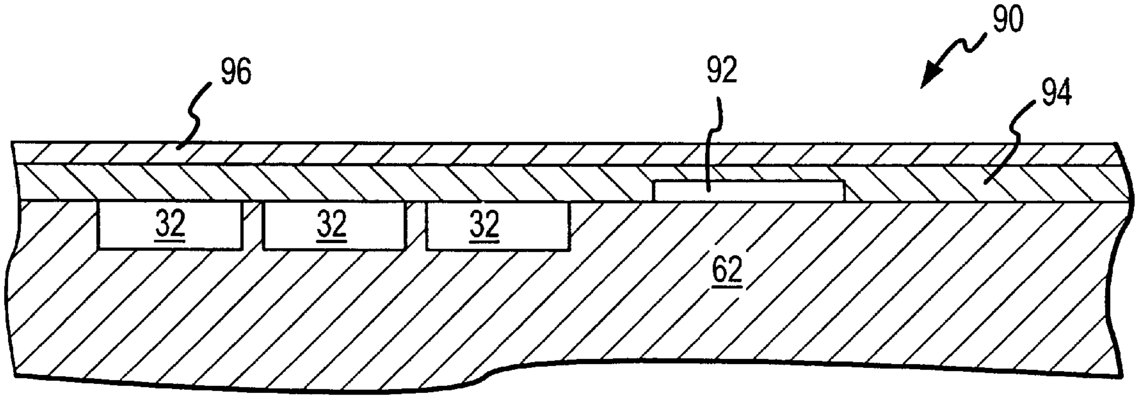
FIG. 15 is a partial cross sectional view of a MUT transducer array according still another embodiment of the invention.

FIG. 15 is a partial cross sectional view of a MUT transducer array 90 according still another embodiment of the invention. The array 90 includes a plurality of MUTs 32 embedded in an acoustic attenuation material 62 that substantially encapsulates the MUTs 32. A layer 94 comprised of a semiconductor material is interposed between a dielectric layer 96 and the plurality of MUTs 32. The dielectric layer 96 may be comprised of a thin layer of silicon dioxide or silicon nitride, although other alternatives exist. The array 90 further includes at least one semiconductor circuit 92 that is monolithically formed in the layer 94 at a location proximate to the plurality of MUTs 32. As described in detail in connection with other embodiments of the invention, the circuit 92 may include a single device, or may comprise more fully integrated devices, including circuits that at least partially perform receiver, beamforming processing, or still other operations. The semiconductor circuit 92 may be interconnected with the plurality of MUTs 32 and to other circuits external to the array by conductive elements formed in the substrate (not shown). Alternatively, at least one circuit 92 may be formed in the layer 94 at a position approximately below the plurality of MUTs 32 and form interconnections (not shown) with the MUTs 32 through vias (also not shown) that extend from the MUTs 32 to the at least one circuit 92.

Fabrication of the array 90 of FIG. 15 may proceed generally as shown in FIGS. 10 through 12. A dielectric layer 96 may be formed on a silicon substrate 34 (as shown in FIG. 10). Alternatively, a silicon-on-insulator (SOI) substrate may be used to provide both the substrate 34 and the dielectric layer 96. In either case, the semiconductor circuits 92 are formed where desired in the layer 94. The MUTs 32 may then be formed in the layer 94 and a surface of the array 90 that includes the MUTs may be covered with the acoustic attenuation material 62. The substrate 34 may then be removed by backgrinding, etching, or other similar methods to yield the array 90 shown in FIG. 15.

Figure 16:
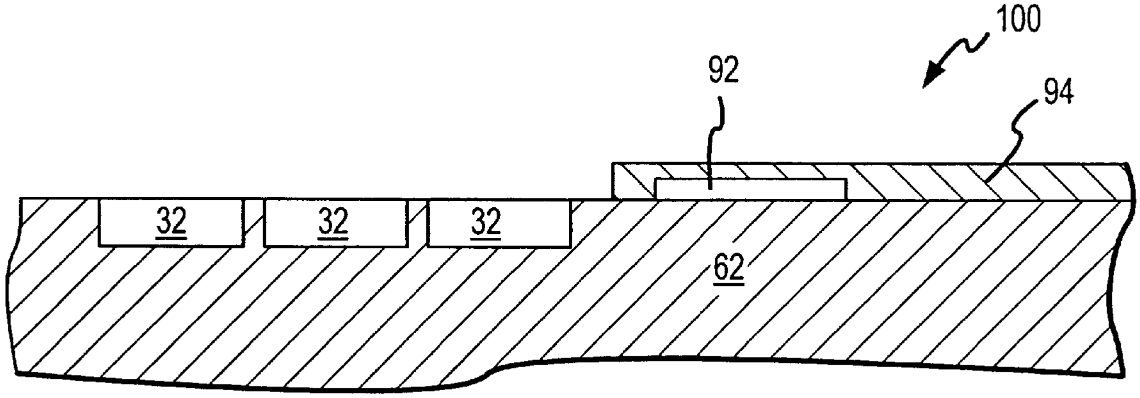
FIG. 16 is a partial cross sectional view of a MUT transducer array according to yet still another embodiment of the invention.

FIG. 16 is a partial cross sectional view of a MUT transducer array 100 according to yet still another embodiment of the invention. The array 100 is similar to the embodiment shown in FIG. 15 with the dielectric layer 96 removed, and at least a portion of the layer 94 removed, or not formed. Since the layer 96 and 94 are removed, acoustic attenuation due to the layers 96 and 94 are largely eliminated, so that the receiving and transmitting abilities of the MUTs 32 is enhanced. In addition, the layer 94 may be left or formed as islands (not shown) that may be used to form additional circuits 92, either adjacent to, or between the MUTs 32.

In addition to the advantages present in other embodiments of the invention, the foregoing embodiments include at least one semiconductor circuit that is monolithically formed in the substrate, and positioned in the substrate at a location proximate to the MUTs. The semiconductor circuit advantageously permits at least a portion of the signal processing and/or control circuits for the MUTs to be formed on a common substrate, resulting in significant cost savings through reduced hardware requirements, and savings in fabrication costs.

The above description of illustrated embodiments of the invention is not intended to be exhaustive or to limit the invention to the precise form disclosed. While specific embodiments of, and examples of, the invention are described in the foregoing for illustrative purposes, various equivalent modifications are possible within the scope of the invention, as those skilled within the relevant art will recognize. For example, the cavity formed behind the MUTs is, as mentioned above, generally filled with an acoustic material, and the filled cavity or the thinned substrate layer are generally backed with acoustic backing material in the form of a layer or backing block having attenuative and impedance characteristics chosen in accordance with the requirements of the particular application. One or the other or both the cavity and backing may alternatively be air-filled, which may be desirable in low frequency applications, or when transmitting acoustic waves into air. The cavity and backing material may have strong attenuative (lossy) properties, or reflective or matching characteristics, depending upon the particular application. Still further, the various embodiments described above can be combined to provide further embodiments. Accordingly, the invention is not limited by the disclosure, but instead the scope of the invention is to be determined entirely by the following claims.

What is claimed is:

1. A micro-machined ultrasonic transducer array, comprising:

a substrate having an upper surface and an opposing lower surface and a thickness there between;

a recess formed in the substrate that projects upwardly into the substrate from the lower surface to an intermediate position within the substrate, the recess being substantially filled with a solid material having a predetermined acoustic property; and at least one micro-machined ultrasonic transducer (MUT) supported by the upper surface of the substrate and positioned over the recess.

2. The array according to claim 1 wherein the MUT is further comprised of a capacitive micro-machined ultrasonic transducer (cMUT).

3. The array according to claim 1 wherein the MUT is further comprised of a piezoelectric micro-machined ultrasonic transducer (pMUT).

4. The array according to claim 1, further comprising a dielectric layer interposed between the substrate and the at least one MUT.

5. The array according to claim 4 wherein the dielectric layer is further comprised of a silicon dioxide layer formed on the substrate.

6. The array according to claim 4 wherein the dielectric layer is further comprised of a silicon nitride layer formed on the substrate.

7. The array according to claim 4, wherein the dielectric layer comprises a silicon oxynitride layer.

8. The array according to claim 1 wherein the recess is further comprised of spaced apart side walls and a top surface positioned between the side walls.

9. The array according to claim 8 wherein the spaced apart sidewalls are angled inwardly to form a tapered recess within the substrate.

10. The array according to claim 8 wherein the top surface is approximately plane-parallel with the upper surface of the substrate.

11. The array according to claim 1 wherein the material is further comprised of an elastomeric material.

12. The array according to claim 1 wherein the material is further comprised of an epoxy resin material.

13. The array according to claim 12 wherein the epoxy resin material is further comprised of an epoxy resin material with a filler material.

14. The array according to claim 1, further comprising a backing member that abuts the lower surface.

15. The array according to claim 1 wherein the substrate is further comprised of at least one semiconductor circuit monolithically formed in the substrate and operatively coupled to the at least one MUT.

16. The array according to claim 15 wherein the at least one semiconductor circuit is further comprised of a circuit formed in a location proximate to the at least one MUT and positioned over the recess.

17. A micro-machined ultrasonic transducer array, comprising:

at least one micro-machined ultrasonic transducer (MUT) formed on a substrate which has been substantially entirely removed; and an acoustic attenuation material of predetermined acoustic properties that substantially encapsulates the at least one MUT.

18. The array according to claim 17 wherein the MUT is further comprised of a capacitive micro-machined ultrasonic transducer (cMUT).

19. The array according to claim 17 wherein the MUT is further comprised of a piezoelectric micro-machined ultrasonic transducer (pMUT).

20. The array according to claim 17 wherein the substrate has been removed up to an etch-stop layer.

21. The array according to claim 20 wherein the etch-stop layer is further comprised of silicon nitride.

22. The array according to claim 20 wherein the etch-stop layer is further comprised of silicon dioxide.

23. The array according to claim 20 wherein the etch-stop layer is further comprised of silicon oxynitride.

24. The array according to claim 17 wherein the acoustic material is further comprised of an elastomeric material.

25. The array according to claim 17 wherein the acoustic material is further comprised of an epoxy resin material.

26. The array according to claim 17 wherein at least one semiconductor circuit is monolithically formed and operatively coupled to the at least one MUT.

27. A method for fabricating a micro-machined ultrasonic transducer array, comprising:

forming at least one micro-machined ultrasonic transducer (MUT) on a surface of a substrate;

removing a portion of the substrate to form a recess that underlies the at least one MUT; and disposing solid acoustic attenuation material into the recess.

28. The method according to claim 27 wherein removing a portion of the substrate further comprises: etching the substrate to form a recess having spaced-apart side walls and a top surface positioned between the side walls.

29. The method according to claim 28 wherein etching the substrate to form a recess further comprises: etching the recess to form a tapered recess within the substrate.

30. The method according to claim 28 wherein etching the substrate further comprises: etching the recess to form a top surface that is approximately parallel with the surface of the substrate.

31. The method according to claim 27 wherein forming at least one micro-machined ultrasonic transducer (MUT) further comprises: forming at least one monolithic semiconductor circuit in the surface of the substrate that is operatively coupled to the at least one MUT.

32. The method according to claim 31 wherein forming at least one monolithic semiconductor circuit in the surface of the substrate further comprises: forming the at least one monolithic semiconductor circuit at a location proximate to the at least one MUT and positioned over the recess.

33. The method according to claim 27 wherein forming at least one micro-machined ultrasonic transducer (MUT) further comprises: forming at least one capacitive micro-machined ultrasonic transducer (cMUT) on a surface of the substrate.

34. The method according to claim 27 wherein forming at least one micro-machined ultrasonic transducer (MUT) further comprises: forming at least one piezoelectric micro-machined ultrasonic transducer (pMUT) on a surface of the substrate.

35. The method according to claim 27 wherein disposing an acoustic attenuation material further comprises: disposing an elastomeric material into the recess.

36. The method according to claim 27 wherein disposing an acoustic attenuation material further comprises: disposing an epoxy resin material into the recess.

37. The method according to claim 27, further comprising positioning an acoustic backing member beneath the substrate.

38. The method according to claim 37 wherein removing the substrate material further comprises: removing the material by backgrinding the substrate material.

39. The method according to claim 38 wherein removing the substrate material further comprises: removing the substrate material by wet etching the material.

40. A method for fabricating a micro-machined ultrasonic array, comprising:

forming at least one micro-machined ultrasonic transducer (MUT) on a substrate material;

depositing an acoustic attenuation material on the substrate that substantially encapsulates the at least one MUT; and removing at least a substantial portion of the substrate material from the acoustic attenuation material and MUT.

41. The method according to claim 40 wherein forming at least one micro-machined ultrasonic transducer (MUT) further comprises: forming at least one monolithic semiconductor circuit in the substrate material that is operatively coupled to the at least one MUT.

42. The method according to claim 40 wherein depositing an acoustic attenuation material on the surface further comprises: depositing an elastomeric material on the surface.

43. The method according to claim 40 wherein depositing an acoustic attenuation material on the surface further comprises: depositing an epoxy resin material on the surface.

44. The method according to claim 40, wherein forming at least one micro-machined ultrasonic transducer (MUT) further comprises: forming at least one micro-machined ultrasonic transducer (MUT) on the surface of a silicon-on-insulator substrate.

45. A micro-machined ultrasonic transducer array, comprising:

at least one micro-machined ultrasonic transducer (MUT) formed on a surface of a planar supporting layer that permits acoustic waves to be transferred to and from the at least one MUT in a direction approximately perpendicular to the surface while suppressing the propagation of acoustic waves laterally in the supporting layer.

46. The transducer array of claim 45, wherein the planar supporting layer is comprises a silicon nitride layer.

47. The transducer array of claim 45, wherein the planar supporting layer is comprises a silicon dioxide layer.

48. The transducer array of claim 45, wherein an acoustic attenuation material substantially encapsulates the at least one MUT.

* * * * *